(12) United States Patent
Hung et al.

(10) Patent No.: US 7,067,052 B2
(45) Date of Patent: Jun. 27, 2006

(54) PROCESS FOR THE PRODUCTION OF REFORMATE HAVING REDUCED ETHYLBENZENE CONTENT

(75) Inventors: Jain-Kai Hung, Houston, TX (US); Thomas H. Colle, Houston, TX (US); Xiaobing Feng, Houston, TX (US); Gary D. Mohr, Houston, TX (US); Krishna Kulai Rao, Kingwood, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 412 days.

(21) Appl. No.: 10/611,183

(22) Filed: Jul. 1, 2003

(65) Prior Publication Data

US 2005/0000859 A1 Jan. 6, 2005

(51) Int. Cl.
*C10G 35/04* (2006.01)
(52) U.S. Cl. .............................. 208/63; 208/64; 208/65; 208/134
(58) Field of Classification Search ................... 208/63, 208/64, 65, 134
See application file for complete search history.

(56) References Cited

U.S. PATENT DOCUMENTS

| 5,705,726 A | 1/1998 | Abichandani et al. |
| 5,865,986 A | 2/1999 | Buchanan et al. ............ 208/65 |
| 5,958,217 A | 9/1999 | Nacamuli et al. |
| 6,028,238 A | 2/2000 | Beck et al. |
| 6,051,744 A | 4/2000 | Nacamuli et al. |

*Primary Examiner*—Thuan D. Dang (57) ABSTRACT

A process for reforming a hydrocarbon feed containing precursors of ethylbenzene, e.g., $C_8$ isoalkane and/or $C_8$ isoalkene precursors of ethylbenzene, that results in the formation of reduced amounts of ethylbenzene. The process is carried out in a catalytic reforming unit comprised of a plurality of operatively connected reactors comprising at least one lead reforming reactor and a tail reforming reactor. The process is carried out by reforming the feed in at least one lead reactor which contains a first reforming catalyst and a catalyst effective for converting ethylbenzene and further reforming the product of the lead reactor in the tail reactor that contains a second reforming catalyst.

44 Claims, 1 Drawing Sheet

Fig. 1

PROCESS FOR THE PRODUCTION OF REFORMATE HAVING REDUCED ETHYLBENZENE CONTENT

BACKGROUND OF THE INVENTION

1. Field of the Invention

This invention relates to a process for reforming a hydrocarbon feed that results in the formation of reduced amounts of ethylbenzene.

2. Description of the Prior Art

Catalytic reforming is one well-known method of producing $C_6$ to $C_8$ aromatic compounds and involves contacting an aliphatic and/or naphthenic hydrocarbon mixture, such as $C_5$-205° C. naphtha cut from a crude oil distillation unit, with a reforming catalyst. Reforming involves a complex series of chemical reactions, including cracking, dehydrocyclization, dehydrogenation, and isomerization, to produce a product mixture containing a wide variety of aromatic compounds, including benzene, toluene, a $C_8$ aromatic fraction (para-xylene, ortho-xylene, meta-xylenes, and ethylbenzene) and heavy aromatics, such as mesitylene, pseudocumene, ethyltoluenes and other $C_9$–$C_{12}$ aromatics.

The $C_8$ aromatic fraction of the reformate can vary quite widely in composition, but will usually contain 10 to 32 wt. percent ethylbenzene in the $C_8$ aromatics and a near equilibrium amount of xylenes. The amount of ethylbenzene formed during reforming will depend on the composition of the naphtha. Of the xylene isomers, para-xylene is of particular value as a large volume chemical intermediate in a number of applications, such as the manufacture of terephthalic acid, which is an intermediate in the manufacturer of polyester.

The individual xylene isomers of the reformate may be separated by appropriate physical methods. Ortho-xylene may be separated by fractional distillation. Para-xylene is usually recovered in high purity from the $C_8$ aromatic fraction by separating the para-xylene from the ortho-xylene, meta-xylene, and ethylbenzene using separation techniques such as fractional crystallization or selective adsorption, e.g., Parex™ process. The meta-xylene and ortho-xylene remaining after the para-xylene separation are isomerized to produce an equilibrium mixture of xylenes. The para-xylene in the mixture is then separated from the meta-xylene and ortho-xylene and the para-xylene depleted-stream is recycled to extinction to the isomerization unit and then to the para-xylene recovery unit until all of the meta-xylene and ortho-xylene are converted and recovered.

Separation or removal of ethylbenzene from xylene streams is frequently difficult and expensive. One technique for ethylbenzene removal involves the dealkylation of the ethylbenzene to benzene and ethylene. The ethylene produced is saturated to ethane using hydrogen in the presence of a hydrogenation catalyst, such as platinum. Another technique for ethylbenzene reduction involves disproportionation to benzene and diethylbenzene. Still another technique for removing ethylbenzene involves converting ethylbenzene to xylenes. Frequently, ethylbenzene conversion is carried out during the isomerization of the para-xylene depleted feedstream. An example of a xylenes isomerization/ethylbenzene conversion process is disclosed in U.S. Pat. No. 4,899,011.

Ethylbenzene can be formed during reforming from $C_8$ naphthenes, $C_8$ isoalkane and/or $C_8$ isoalkene precursors of ethylbenzene. Examples of such precursors include ethyl-cyclohexane, ethyl-cyclohexenes, 3-ethylhexane, 3-ethylhexenes, 3-ethylhexadienes, 3-ethylhexatriene, 3-methyl-heptane, 3-methylheptenes, 3-methylheptadienes, 3-methylheptatrienes, octane, octenes, octadienes, octatrienes, and/or octatetraenes. The concentration of these precursors in the feed fed to the reformer will affect the amount of ethylbenzene formed during reforming. Generally, the feed will contain from about 1 to about 10 weight percent of ethylbenzene precursors.

The concentration of ethylbenzene in the reformate can affect the efficiency of subsequent xylenes processing operations e.g., para-xylene separation and xylenes isomerization. For example, the processing of a $C_8$ aromatics feed containing 20 weight percent ethylbenzene can result in the total recycle stream to the para-xylene separation unit being increased by about 20 percent over a $C_8$ aromatics feed containing no ethylbenzene. The same increase in recycle stream applies to the xylenes isomerization unit. Thus, the use of a $C_8$ aromatics feed having no ethylbenzene in place of one having 20 percent, can debottleneck subsequent xylenes processing units, e.g., xylenes separation units and isomerization units, by about 20 percent.

In modern isomerization units where the ethylbenzene is dealkylated to benzene in the isomerization unit, the ethylbenzene dealkylation reaction usually proceeds at 50 to 85 percent ethylbenzene conversion per pass. Thus, the recycle feed stream provided to the xylenes separation unit always contains a substantial amount of ethylbenzene. This ethylbenzene builds up in the recycled feed stream causing processing equipment to be larger than necessary to merely process the xylenes. Thus, it is usually desirable that the feed to the isomerization unit have reduced amounts of ethylbenzene. The ethylbenzene contained within the recycle stream can be reduced by operating at high ethylbenzene conversions, but high ethylbenzene conversion is usually accompanied by high conversion of xylenes to less desirable toluene and $C_{9+}$ aromatics. Commercially, an economic optimum ethylbenzene conversion is most often targeted that balances recycle rate and byproduct formation.

The present invention provides a method of reforming a hydrocarbon feed that results in the formation of reformate having reduced amounts of ethylbenzene. By achieving reduced ethylbenzene in the xylenes recovery loop, low byproduct yield can be achieved without substantial buildup of ethylbenzene in the xylenes recovery loop and a commensurate reduction of para-xylene production capacity.

SUMMARY OF THE INVENTION

In accordance with the present invention, there is provided a process for producing a reformate having reduced ethylbenzene content, said process comprising the steps of:

(a) introducing a hydrocarbon feed containing precursors of ethylbenzene, e.g., $C_8$ isoalkane and/or $C_8$ isoalkene precursors of ethylbenzene, into a catalytic reforming unit comprised of a plurality of operatively connected reactors comprising at least one lead reactor and a tail reactor;

(b) reforming said feed in said at least one lead reactor and in the presence of a first reforming catalyst effective for reforming said feed and a catalyst effective for converting ethylbenzene; and, (c) further reforming at least a portion of the product of step (b) in said tail reactor under conversion conditions and in the presence of a second reforming catalyst.

The practice of the invention will usually result in the conversion of at least 25 weight percent of the ethylbenzene formed during reforming of the feed. Preferably, at least 40 weight percent of the ethylbenzene formed during reforming is converted and, more preferably, at least 50 weight percent of the ethylbenzene formed during reforming is converted.

DETAILED DESCRIPTION OF THE INVENTION

Reforming

Substantially any conventional feedstock can be utilized. Typical feedstocks that can be used in the present invention includes $C_6$–$C_{20}$ hydrocarbon or hydrocarbon mixtures, such as a $C_5$-205° C. naphtha, e.g., $C_5$–$C_{12}$ hydrocarbons such as $C_5$–$C_{12}$ paraffin mixtures, and/or $C_6$–$C_8$ alcohol or alcohol mixtures. The feedstock will usually include $C_6$+ paraffinic feeds, and will preferably contain $C_6$–$C_8$ hydrocarbons. To take advantage of the benefits of the invention, the feed will contain $C_8$ isoalkane and/or $C_8$ isoalkene precursors of ethylbenzene. The precursors are usually present in the feedstock in an amount in the range of from about 1 to about 10 weight percent based on the weight of the feed. Preferably, the precursors are present in the feedstock in an amount in the range of from about 1 to about 5 weight percent based on the weight of the feed. Preferred feeds are $C_6$–$C_8$ hydrocarbon feeds, especially when the reforming catalyst is a monofunctional catalyst. The reforming is carried out by contacting the feed with a reforming catalyst under reforming conditions to produce a reaction product usually comprising aromatics and paraffins. The reformate is formed under typical reforming conditions designed to promote dehydrogenation of naphthenes, isomerization of paraffinic hydrocarbons and dehydrocyclization of non-aromatic hydrocarbons.

Catalysts suitable for use in catalytic reforming include acidic reforming catalysts (bifunctional catalysts) and non-acidic reforming catalysts (monofunctional catalysts).

Bifunctional reforming catalysts usually comprise a metallic oxide support having disposed therein one or more Group VIII metals, e.g., platinum, palladium, iridium, ruthenium, osmium, or nickel. Suitable metallic oxide supports include alumina, silica, and silica-alumina. Preferably, the bifunctional reforming catalyst comprises a metallic oxide support having disposed therein in intimate admixture a Group VIII metal (preferably platinum). One or more promotor elements, such as rhenium, tin, germanium, cobalt, nickel, iridium, rhodium, ruthenium, may also be included. More preferably, the bifunctional reforming catalyst comprises an alumina support, platinum and rhenium or platinum and tin on an alumina support. The acidic sites are preferably provided by the presence of a halogen, such as chlorine.

Non-acidic or monofunctional reforming catalysts will comprise a non-acidic molecular sieve, e.g., zeolite, and one or more hydrogenation/dehydrogenation components. The molecular sieve will preferably have a pore size from about 5 to about 8 Å and the framework atoms will include at least one element, usually two elements, selected from the group consisting of Si, Al, P, Ge, Ga and Ti. These molecular sieves are described in "Atlas of Zeolite Framework Types", eds. Ch. Baerlocher, W. H. Meier, and D. H. Olson, Elsevier, Fifth Edition, 2001, which is hereby incorporated by reference, and include, for example, LTL, FAU, *BEA, AEL, PAU, MAZ, MFI, MEL, MTW, OFF, EMT, MOR, MFS, EUO, MTT, HEU, FER, TON, and AFI structure types. Examples of specific molecular sieves include Silicalite 1, Silicalite 2, ALPO-5, zeolite L, zeolite X, zeolite Beta, zeolite Y, ETAS-10, ETGS-10, and ETS-10. The most preferred large pore molecular sieve is zeolite L. Binderless aggregates of Zeolite L of the type disclosed in U.S. Pat. No. 5,849,967 may also be used in the process.

The exchangeable cations of the molecular sieve may be one or more metals selected from the group consisting of alkali metals and alkaline earth metals. Preferably, the exchangeable cation comprises one or more alkali metals, e.g., potassium, which can be partially or substantially fully exchanged with one or more alkaline earth metals.

The monofunctional catalysts will contain one or more hydrogenation/dehydrogenation metals, e.g., Group VIIB metals, such as rhenium, and Group VIII metals, such as platinum, palladium, iridium, ruthenium, osmium, nickel or rhodium. The preferred Group VIII metal is platinum. Also, the non-acidic catalysts can contain a metal promoter such as tin.

The amount of hydrogenation/dehydrogenation metal present on the monofunctional catalyst will usually be from about 0.1% to about 5% by weight based on the weight of the catalyst. The metal can be incorporated into the molecular sieve during synthesis of the molecular sieve, by impregnation, or by ion exchange of an aqueous solution containing the appropriate salt. By way of example, in an ion exchange process, platinum can be introduced by using cationic platinum complexes such as tetraammine-platinum (II) nitrate.

The monofunctional catalyst will usually include a binder. The binder can be a natural or a synthetically produced inorganic material such as inorganic oxides. Typical supports which can be used include clays, alumina, and silica, in which acidic sites are preferably exchanged by cations that do not impart strong acidity. The molecular sieve may also be composited with molecular sieve materials such as the materials disclosed in U.S. Pat. No. 5,993,642, which is hereby incorporated by reference.

The reforming process can be continuous, cyclic or semi-regenerative. The process can be in a fixed bed, moving bed, tubular, radial flow or fluidized bed.

Conditions for reforming include temperatures of at least about 300° C. to about 600° C. and pressures from about 50 psig (446 kPa) to about 500 psig (3,549 kPa), a mole ratio of hydrogen to hydrocarbons from about 0.1:1 to about 10:1 and a liquid hour space velocity of between about 1 and about 10.

Ethylbenzene Removal

The process of this invention is not limited to any particular mode for the conversion of ethylbenzene. Any reaction leading to the destruction or conversion of ethylbenzene, e.g., the dealkylation of ethylbenzene, the disproportionation of ethylbenzene, and the conversion of ethylbenzene to xylenes, is referred to herein as "ethylbenzene conversion".

As used herein, the expression "reformate having reduced ethylbenzene content" shall mean that at least 25 percent of the ethylbenzene formed during the reforming is converted to a different product, such as benzene or xylenes. Preferably, at least 40 percent of the ethylbenzene formed during the reforming is converted to a different product.

The ethylbenzene conversion catalyst will located in one or more of the lead reactors and can be any catalyst capable of converting the ethylbenzene to another product.

Preferred catalysts for converting ethylbenzene include molecular sieves having a pore size greater than 5 Å, such as large pore and intermediate pore size molecular sieves. A large pore molecular sieve generally has a pore size of at least about 7 Å. Examples of suitable large pore molecular sieves include MAZ, FAU, EMT, OFF, *BEA, and MOR structure types (IUPAC Commission of Zeolite Nomenclature). Examples of large pore molecular sieves include mazzite, offretite and mordenite. An intermediate pore size molecular sieve generally has a pore size from about 5 Å to about 7 Å and include, for example, AEL, MFI, MEL, MFS, MEI, MTW, EUO, MTT, HEU, FER, and TON structure types. Examples of such molecular sieves include ZSM-5, ZSM-11, ZSM-22, ZSM-23, ZSM-48, ZSM-50, ZSM-57, ZSM-58, EU-1, NU-87, SAPO-11, and SAPO-41.

The intermediate pore size molecular sieves will preferably have a composition having the following molar relationship:

$$X_2O_3 : (n)YO_2,$$

wherein X is a trivalent element, such as aluminum, boron and/or gallium, Y is a tetravalent element such as silicon, tin, and/or germanium; and n has a value greater than 10, said value being dependent upon the particular type of molecular sieve and the trivalent element present in the molecular sieve. When the intermediate pore size molecular sieve has a MFI structure type, n is preferably greater than 20. Preferably, the intermediate pore size molecular sieve is an aluminosilicate zeolite.

When the intermediate pore size molecular sieve is a gallosilicate molecular sieve, the molecular sieve preferably comprises a composition having the following molar relationship:

$$Ga_2O_3 : ySiO_2$$

wherein y is between about 24 and about 500. The molecular sieve framework may contain only gallium and silicon atoms or may also contain a combination of gallium, aluminum, and silicon.

If the mode of ethylbenzene conversion involves the dealkylation of ethylbenzene, the molecular sieve employed in ethylbenzene conversion preferably has a relatively high acid activity, as measured by having an alpha value of at least 50, more typically of about 100 to about 500 and preferably of about 100 to about 300. If the mode of ethylbenzene conversion involves converting the ethylbenzene to xylenes, the molecular sieve employed in ethylbenzene conversion preferably has a relatively low acid activity, as measured by having an alpha value of less than 50, more typically of about 0.1 to about 30 and preferably of about 0.5 to about 10. The alpha test is described in U.S. Pat. No. 3,354,078; in the *Journal of Catalysis*, Vol. 4, p. 527 (1965); Vol. 6, p. 278 (1966); and Vol. 61, p. 395 (1980), each incorporated herein by reference as to that description. The experimental conditions of the test used herein include a constant temperature of 538° C. and a variable flow rate as described in detail in the *Journal of Catalysis*, Vol. 61, p. 395.

Molecular sieves having an intermediate pore size molecular sieve and unidimensional 10-membered ring pores can be used to isomerize the ethylbenzene in the feed selectively to para-xylene. Examples of such molecular sieves include ZSM-11, ZSM-22, ZSM-23, ZSM-48, ZSM-50, ZSM-57, SAPO-11, SAPO-41, and NU-87.

The ethylbenzene conversion catalyst will usually contain at least one hydrogenation metal. Examples of such metals include the oxide, hydroxide, sulfide, or free metal (i.e., zero valent) forms of Group VIII metals (i.e., Pt, Pd, Ir, Rh, Os, Ru, Ni, Co, and Fe), Group IVA metals (i.e., Sn and Pb), Group VA metals (i.e., Sb and Bi), and Group VIIB metals (i.e., Mn, Tc, and Re). Noble metals (i.e., Pt, Pd, Ir, Rh, Os, and Ru) are preferred. Combinations of catalytic forms of noble or non-noble metals, such as combinations of Pt with Ni, may be used. The metal is preferably in a reduced valence state. The reduced valence state of the metal may be attained, in situ, during the course of the reaction, when a reducing agent, such as hydrogen, is included in the feed to the reaction. Treatments such as coking or sulfiding may also be employed, especially at the start of a run with fresh catalyst, to modify the catalytic performance of the metal.

The amount of metal present in the catalyst will be an effective amount which will generally be from about 0.001 to about 10 percent by weight and, preferably 0.01 to 3.0 percent by weight. The amount will vary with the nature of the metal, less of the highly active metals, particularly platinum, being required than of the less active metals.

The hydrogenation metal may be incorporated into the molecular sieve using techniques known to persons skilled in the art such as by ion exchange or impregnation.

In addition, it may be desirable to combine the molecular sieve with another material resistant to the temperature and other conditions of the process. Such matrix materials include synthetic or naturally occurring substances as well as inorganic materials such as clay, silica, and/or metal oxides. The metal oxides may be naturally occurring or in the form of gelatinous precipitates or gels including mixtures of silica and metal oxides. Naturally occurring clays which can be composited with the molecular sieve include those of the montmorillonite and kaolin families, which families include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the molecular sieves employed herein may be composited with a porous matrix material, such as alumina, silica-alumina, silica-magnesia, silica-zirconia, silica-thoria, silica-berylia, silica-titania, as well as ternary compounds such as silica-alumina-thoria, silica-alumina-zirconia, silica-alumina-magnesia, and silica-magnesia-zirconia. A mixture of these components could also be used. The matrix may be in the form of a cogel. Further, the molecular sieve may also be composited with molecular sieve materials, such as binder particles of molecular sieve.

The relative proportions or amount of molecular sieve and matrix material on an anhydrous basis may vary widely with the molecular sieve content usually ranging from between about 1 to about 99 percent by weight and more usually in the range of about 10 to about 80 percent by weight based on the weight of the catalyst. Catalysts particularly suited for the ethylbenzene conversion are zeolite bound zeolite catalysts. These catalysts, as well as their method of preparation, are described in U.S. Pat. No. 6,008,425, which is hereby incorporated by reference. The zeolite bound zeolite catalysts will comprise first crystals of an acidic intermediate pore size first molecular sieve, a binder comprising second crystals of a second molecular sieve, and a hydrogenation metal. Preferably, the zeolite bound zeolite catalyst contains less than 10 percent by weight of non-zeolitic binder, e.g., amorphous binder, based on the total weight of the first and second zeolite. An example of such a catalyst comprises first crystals of a MFI or MEL structure type, e.g., ZSM-5 or ZSM-11, a binder comprising second crystals of MFI or MEL structure type, e.g., Silicalite 1 or Silicalite 2, and at least one Group VIII metal.

To make the molecular sieve selective to the production of para-xylene (versus the other xylene isomers) and/or to reduce reactions on the surface of the molecular sieve, the molecular sieve catalyst, e.g., ZSM-5 catalyst, can be selectivated by the use of a selectivating agent. The term "selectivating agent" is used herein to indicate substances which will increase the shape-selectivity (i.e., para-selectivity) of the catalyst.

Examples of compounds for selectivating the catalysts include treating the surface of the catalyst with compounds of phosphorus and/or various metal oxides such as alkaline earth metal oxides, e.g., calcium oxide, magnesium oxide, etc. rare earth metal oxides, lanthanum oxide, and other metal oxides such as boron oxide, titania, antimony oxide, silica, and manganese oxide.

Selectivation may also be accomplished by depositing coke on the catalyst. For example, the catalyst can be preselectivated with coke such as by exposing the catalyst in the reactor to a thermally decomposable organic compound, e.g., benzene, toluene, etc. at a temperature in excess of the decomposition temperature of said compound, e.g., from about 400° C. to about 650° C., more preferably 425° C. to about 550° C., at a WHSV in the range of from about 0.1 to about 20 lbs. of feed per pound of catalyst per hour, at a pressure in the range of from about 1 to about 100 atmospheres, and in the presence of 0 to about 2 moles of hydrogen, more preferably from about 0.1 to about 1 moles of hydrogen per mole of organic compound, and optionally in the presence of 0 to about 10 moles of nitrogen or another inert gas per mole of organic compound. This process is conducted for a period of time until a sufficient quantity of coke has deposited on the catalyst surface, generally at least about 2% by weight and more preferably from about 8 to about 40% by weight of coke.

Selectivation of the catalyst may also be accomplished using organosilicone compounds. The silicon compounds may comprise a polysiloxane include silicones, a siloxane, and a silane including disilanes and alkoxysilanes.

Silicone compounds that can be used in the present invention include the following:

wherein $R_1$ is hydrogen, fluoride, hydroxy, alkyl, aralkyl, alkaryl or fluoro-alkyl. The hydrocarbon substituents generally contain from 1 to about 10 carbon atoms and preferably are methyl or ethyl groups. $R_2$ is selected from the same group as $R_1$, and n is an integer of at least 2 and generally in the range of 2 to about 1000. The molecular weight of the silicone compound employed is generally between about 80 to about 20,000 and preferably about 150 to about 10,000. Representative silicone compounds include dimethylsilicone, diethylsilicone, phenylmethylsilicone, methyl hydrogensilicone, ethylhydrogensilicone, phenylhydrogensilicone, fluoropropylsilicone, ethyltrifluoroprophysilicone, tetrachlorophenyl methyl methylethylsilicone, phenylethylsilicone, diphenylsilicone, methyltrisilicone, tetrachlorophenylethyl silicone, methylvinylsilicone and ethylvinylsili-cone. The silicone compound need not be linear but may be cyclic as for example hexamethylcyclotrisiloxane, octamethylcyclotetrasiloxane, hexaphenyl cyclotrisiloxane and octaphenylcyclotetrasiloxane. Mixtures of these compounds may also be used as well as silicones with other functional groups.

Useful siloxanes and polysiloxanes include as non-limiting example hexamethylcyclotrisiloxane, octamethylcyclotetrasiloxane, decamethyl cyclopentasiloxane, hexamethyldisiloxane, octamethytrisiloxane, decamethyltetrasiloxane, hexaethylcyclotrisiloxane, octaethylcyclo tetrasiloxane, hexaphenylcyclotrisiloxane and octaphenylcyclo-tetrasiloxane.

Useful silanes, disilanes, or alkoxysilanes include organic substituted silanes having the general formula:

wherein R is a reactive group such as hydrogen, alkoxy, halogen, carboxy, amino, acetamide, trialkylsilyloxy, $R_1$, $R_2$ and $R_3$ can be the same as R or can be an organic radical which may include alkyl of from 1 to about 40 carbon atoms, alkyl or aryl carboxylic acid wherein the organic portion of alkyl contains 1 to about 30 carbon atoms and the aryl group contains about 6 to about 24 carbons which may be further substituted, alkylaryl and arylalkyl groups containing about 7 to about 30 carbon atoms. Preferably, the alkyl group for an alkyl silane is between about 1 and about 4 carbon atoms in chain length. Mixtures may also be used.

The silanes or disilanes include, as non-limiting examples, dimethylphenylsilane, phenytrimethylsilane, triethylsilane and hexamethyldislane. Useful alkoxysilanes are those with at least one silicon-hydrogen bond.

Selectivation of the catalyst can also be accomplished using a combination of coke, metal oxides, phosphorus compounds, and silicon applied by the procedures described above.

Typically, the temperature and pressure conditions established for reforming are not modified for the ethylbenzene conversion. Usually, the ethylbenzene conversion is maintained at temperatures ranging from about 300° C. to about 600° C., usually above about 320° C. to 550° C., more specifically above about 350° C. to about 510° C. Appropriate pressures are, usually, greater than atmospheric, above about 239 kPa, specifically above about 446 kPa up to about 6996 kPa, specifically, about 791 kPa which are compatible with the conditions of the reformer. Typically, because the feed contains hydrogen, the reaction is conducted in the presence of hydrogen. The hydrogen to hydrocarbon mole ratio can range from about 0.1 to about 10. Hydrogen can be added as quench to control the reaction. The catalyst space velocity is, typically, less than about 75 WHSV, more typically less than about 50 WHSV, even more typically from about 5 to about 30 WHSV.

Figure 1:
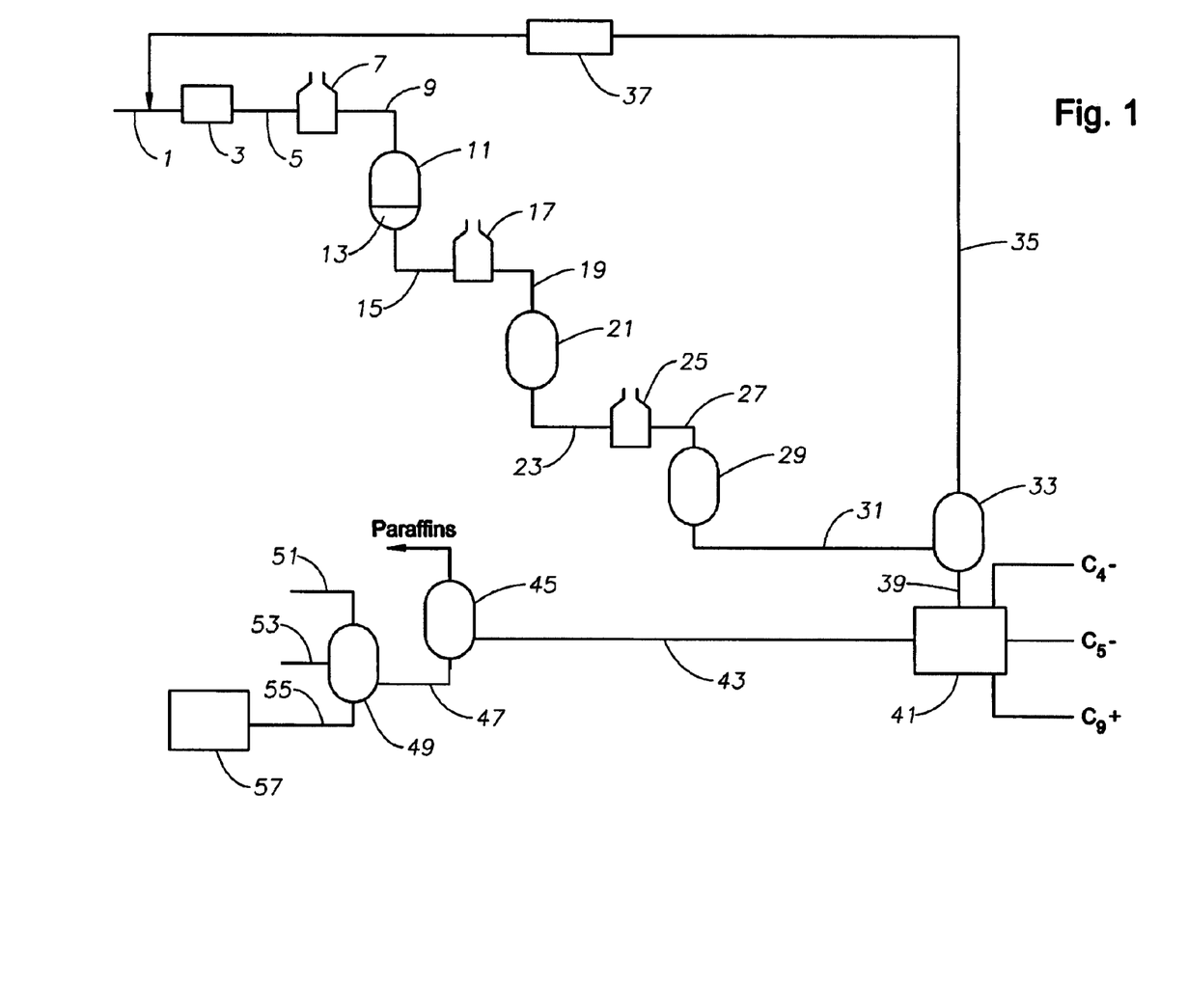
FIGURE is a simplified schematic flow diagram, illustrating an embodiment of the invention.

The FIGURE is a simplified schematic flow diagram of a non-limiting embodiment of the invention. Referring to the FIGURE, a petroleum naphtha is directed via line 1 to heat exchanger 3 where the temperature of the naphtha is elevated. Next, the heated naphtha is sent via line 5 to reformer heater 7 which elevates the temperature of the feed to a temperature suitable for reforming. The heated feed is charged to a plurality of reformer reactors 11, 21, and 29 with interstage heaters 17 and 25. Although three reformer reactors are shown, there can be two reactors or more than three reactors. In this embodiment, reformer reactors 11 and 21 are lead reactors as they are located upstream from reformer reactor 29, the tail reactor. The lead reactors are those reactors located upstream from the tail reactor. In the case of a system employing only two reactors, the upstream reactor is the lead reactor and the downstream reactor is the tail reactor. The bottom portion 13 of the first reformer reactor 11 is loaded with the ethylbenzene conversion catalyst. The ethylbenzene conversion catalyst is not limited to any mode of ethylbenzene conversion, e.g., conversion of ethylbenzene by dealkylation or conversion of ethylbenzene to xylenes. The feed passes over the ethylbenzene conversion catalyst before it exits the first reformer reactor 11 to produce a product of reduced ethylbenzene content as compared to a product not passed over the ethylbenzene conversion. Usually the reformate is cascaded over the ethylbenzene conversion catalyst.

After leaving the first reactor 11 via line 15, the product is reheated to reforming temperature in heater 17 and then sent to via line 19 to second reformer reactor 21. Although not shown in the FIGURE, the second reformer reactor 21 can also contain an ethylbenzene conversion catalyst. Alternatively, second reformer reactor 21 can contain ethylbenzene conversion catalyst while first reformer reactor 11 does not contain any ethylbenzene conversion catalyst. If both lead reactors contain an ethylbenzene conversion catalyst, each catalyst can have a different mode of ethylbenzene conversion. For example, the catalyst of the first lead can have an ethylbenzene conversion catalyst for converting the ethylbenzene to xylenes and the catalyst of the second lead reactor can contain an ethylbenzene conversion catalyst that dealkylates the ethylbenzene.

It has been found that in a reforming unit with a plurality of reforming reactors, the concentration of ethylbenzene is highest in the lead reactors. Locating the ethylbenzene conversion catalyst in at least one lead reactor (versus the downstream tail reactor) results in greater amounts of ethylbenzene being converted. Also, if the ethylbenzene conversion catalyst is a catalyst that converts the ethylbenzene to xylenes, locating the ethylbenzene conversion catalyst in the at least one lead reactor results in greater para-xylene formation.

After leaving the second reforming reactor via line 23, the product is reheated to reforming temperature in heater 25 and then sent via line 27 to third reformer reactor 29. The aromatics rich product is passed via line 31 to vapor/liquid separator 33 which separates a hydrogen-rich gas via hydrogen compressor 37 via line 35 for recycling to the reformer via line 1. Via line 39, the liquid product is conveyed from separator 33 to fractionator 41 to separate the product into $C_4$-, $C_5$-, $C_6$ to $C_8$, and $C_{9+}$. The $C_{9+}$ can be separated and recycled to the reformer reaction zone. The $C_6$ to $C_8$ stream of fractionator 41 is transferred by line 43 to a paraffin separator 45 which separates the paraffins from the aromatics, typically, by solvent extraction. The aromatics extract is then be conveyed via line 47 to separation zone 49 and benzene is removed via line 51, toluene is removed via line 53 and xylenes are removed via line 55 and converted to the desired products, e.g., para-xylene, in xylenes loop 57.

The following examples are illustrative of the invention.

EXAMPLE 1

The following example is a computer simulation of the process of the present invention. The catalyst used in this example is a catalyst that converts ethylbenzene to equilibrium amounts of xylenes. The ethylbenzene conversion catalyst is located in the lead reactor.

Simulation results were obtained using Pro II Version 5.5 Software from Simulation Services Inc. Vapor pressure measurements were converted into equilibrium vapor and liquid compositions using an activity coefficient model, i.e., the Non-Random, Two-Liquid (NRTL) method.

Reaction stoichiometry used for the simulation is the following:

Ethylbenzene→para-xylene+meta-xylene+ortho-xylene

In the process simulation, the reforming catalyst reforms the naphtha feed to an intermediate product, which feeds to the ethylbenzene conversion catalyst to convert ethylbenzene to an equilibrium amount of ethylbenzene and mixed xylenes.

The simulation is carried out under typical reforming conditions, e.g, 200 psig, 950 F, $H_2$:Oil=1.37, and WHSV=2 $h^{-1}$.

Table 1 below summarizes the stream component flow rates of the simulation. All flow rates are in Pound-Mole/Hour.

TABLE 1

| | Component Rates | | |
|---|---|---|---|
| Stream Name<br>Description<br>Phase | PROD<br>End Reforming<br>Catalyst in R1<br>Vapor | PROD<br>End Reforming<br>Catalyst in R1<br>Vapor | PROD<br>End Reforming<br>Catalyst in R4<br>Vapor |
| Molecular Weight | 950.000 | 950.000 | 950.000 |
| | 214.696 | 214.696 | 214.696 |
| | 39.643 | 39.643 | 39.643 |
| Component Molar Rates   LB-MOL/HR | | | |
| Hydrogen | 304.921 | 304.921 | 321.921 |
| Ethylbenzene | 10.000 | 5.015 | 6.015 |
| Para-xylene | 10.303 | 11.701 | 15.701 |
| Meta-xylene | 23.609 | 26.003 | 34.003 |

TABLE 1-continued

| | | Component Rates | | |
|---|---|---|---|---|
| Stream Name | | PROD | PROD | PROD |
| Description | | End Reforming Catalyst in R1 | End Reforming Catalyst in R1 | End Reforming Catalyst in R4 |
| Phase | | Vapor | Vapor | Vapor |
| Ortho-xylene | | 11.809 | 13.001 | 17.001 |
| Others | | 166.971 | 166.971 | 149.971 |
| Total | LB-MOL/HR | 527.612 | 527.612 | 544.612 |

EXAMPLE 2 (COMPARATIVE)

The following example is a computer simulation of a process where the ethylbenzene conversion catalyst is located in the tail reactor. The simulation is carried in the same manner as Example 1, except that the ethylbenzene conversion catalyst is located in the tail reactor.

Table 2 below summarizes the stream component flow rates of the simulation. All flow rates are in Pound-Mole/Hour.

TABLE 2

| | | Component Rates | | |
|---|---|---|---|---|
| Stream Name | | PROD | PROD | PROD |
| Description | | End Reforming Catalyst in R1 | End Reforming Catalyst in R4 | End Reforming Catalyst in R4 |
| Phase | | Vapor | Vapor | Vapor |
| Molecular Weight | | 950.000 | 950.000 | 950.000 |
| | | 214.696 | 214.696 | 214.696 |
| | | 39.643 | 39.643 | 39.643 |
| Component Molar Rates | LB-MOL/HR | | | |
| Hydrogen | | 304.921 | 321.921 | 304.921 |
| Ethylbenzene | | 10.000 | 11.000 | 6.545 |
| Para-xylene | | 10.303 | 14.303 | 15.271 |
| Meta-xylene | | 23.609 | 31.609 | 33.936 |
| Ortho-xylene | | 11.809 | 15.809 | 16.968 |
| Others | | 166.971 | 149.971 | 149.971 |
| Total | LB-MOL/HR | 527.612 | 544.612 | 527.612 |

In comparing with Example 1, the results show that when the ethylbenzene conversion catalyst is located in a tail reactor (versus lead reactor), the resulting reform ate contains greater amounts of ethylbenzene.

EXAMPLE 3

The following example is a computer simulation of the process of the present invention. The software used in the simulation is the same as Example 1. The catalyst used in the simulation is an ethylbenzene to equilibrium para-xylene catalyst. The catalyst is located in the lead reactor.

Reaction stoichiometry used for the simulation is the following:

Ethylbenzene→para-xylene

In the process simulation, the reforming catalyst reforms the naphtha feed to an intermediate product, which feeds to an ethylbenzene conversion catalyst to convert ethylbenzene to equilibrium amounts of ethylbenzene and para-xylene.

The simulation is carried out under typical reforming conditions, e.g, 200 psig, 950 F, $H_2$:Oil=1.37, and WHSV=2 $h^{-1}$.

Table 3 below summarizes the stream component flow rates. All flow rates are in Pound-Mole/Hour.

TABLE 3

| | Component Rates | | |
|---|---|---|---|
| Stream Name | PROD | PROD | PROD |
| Description | End Reforming Catalyst in R1 | End Reforming Catalyst in R4 | End Reforming Catalyst in R4 |
| Phase | Vapor | Vapor | Vapor |
| Molecular Weight | 950.000 | 950.000 | 950.000 |
| | 214.696 | 214.696 | 214.696 |
| | 39.643 | 39.643 | 39.643 |

TABLE 3-continued

| | | Component Rates | | |
|---|---|---|---|---|
| Stream Name | | PROD | PROD | PROD |
| Component Molar Rates | LB-MOL/HR | | | |
| Hydrogen | | 304.921 | 304.921 | 321.921 |
| Ethylbenzene | | 10.000 | 5.725 | 6.725 |
| Para-xylene | | 10.303 | 14.577 | 18.577 |
| Meta-xylene | | 23.609 | 23.609 | 31.609 |
| Ortho-xylene | | 11.809 | 11.809 | 15.809 |
| Others | | 166.971 | 166.971 | 149.971 |
| Total | LB-MOL/HR | 527.612 | 527.612 | 544.612 |

EXAMPLE 4 (COMPARATIVE)

The following example is a computer simulation of a process where the ethylbenzene conversion catalyst is located in the tail reactor. The simulation is carried in the same manner as Example 3, except that the ethylbenzene conversion catalyst is located in the tail reactor.

Table 4 below summarizes the stream component flow rates of the simulation. All flow rates are in Pound-Mole/Hour.

TABLE 4

| | | Component Rates | | |
|---|---|---|---|---|
| Stream Name | | PROD | PROD | PROD |
| Description | | End Reforming Catalyst in R1 | End Reforming Catalyst in R4 | End Reforming Catalyst in R4 |
| Phase | | Vapor | Vapor | Vapor |
| Molecular Weight | | 950.000 | 950.000 | 950.000 |
| | | 214.696 | 214.696 | 214.696 |
| | | 39.643 | 39.643 | 39.643 |
| Component Molar Rates | LB-MOL/HR | | | |
| Hydrogen | | 304.921 | 321.921 | 304.921 |
| Ethylbenzene | | 10.000 | 11.000 | 7.135 |
| Para-xylene | | 10.303 | 14.303 | 18.167 |
| Meta-xylene | | 23.609 | 31.609 | 31.609 |
| Ortho-xylene | | 11.809 | 15.809 | 15.809 |
| Others | | 166.971 | 149.971 | 149.971 |
| Total | LB-MOL/HR | 527.612 | 544.612 | 527.612 |

In comparing with Example 3, the results show that when the ethylbenzene conversion catalyst is located in the tail reactor (versus the lead reactor), the resulting reformate contains greater amounts of ethylbenzene.

EXAMPLE 5

The following example is a computer simulation of the process of the present invention. The software used in the simulation is the same as Example 1. The catalyst used in the simulation is an ethylbenzene to benzene and ethane catalyst. The catalyst is located in the lead reactor.

Reaction stoichiometry used for the simulation is the following:

Ethylbenzene→benzene+ethane

In the process simulation, the reforming catalyst reforms the naphtha feed to an intermediate product, which feeds to an ethylbenzene conversion catalyst to convert ethylbenzene to benzene and ethane. The conversion is proportional to the ethylbenzene concentration in the molecular sieve channels, which is dominated by ethylbenzene and para-xylene.

The simulation is carried out under typical reforming conditions, e.g, 200 psig, 950 F, $H_2$:Oil=1.37, and WHSV=2 $h^{-1}$.

Table 5 below summarizes the stream component flow rates. All flow rates are in Pound-Mole/Hour.

TABLE 5

| | Component Rates | | |
|---|---|---|---|
| Stream Name | PROD | PROD | PROD |
| Description | End Reforming Catalyst in R1 | End Reforming Catalyst in R4 | End Reforming Catalyst in R4 |
| Phase | Vapor | Vapor | Vapor |

TABLE 5-continued

| | | Component Rates | | |
|---|---|---|---|---|
| Stream Name | | PROD | PROD | PROD |
| Molecular Weight | | 950.000 | 950.000 | 950.000 |
| | | 214.696 | 214.696 | 214.696 |
| | | 39.643 | 39.643 | 39.643 |
| Component Molar Rates | LB-MOL/HR | | | |
| Hydrogen | | 304.921 | 304.921 | 321.921 |
| Ethylbenzene | | 10.000 | 5.075 | 6.075 |
| Para-xylene | | 10.303 | 10.303 | 14.303 |
| Meta-xylene | | 23.609 | 23.609 | 31.609 |
| Ortho-xylene | | 11.809 | 11.809 | 15.809 |
| Others | | 166.971 | 171.897 | 154.897 |
| Total | LB-MOL/HR | 527.612 | 527.612 | 544.612 |

EXAMPLE 6 (COMPARATIVE)

The following example is a computer simulation of a process where the ethylbenzene conversion catalyst is located in the tail reactor. The simulation is carried in the same manner as Example 5, except that the ethylbenzene conversion catalyst is located in the tail reactor.

Table 6 below summarizes the stream component flow rates of the simulation. All flow rates are in Pound-Mole/Hour.

TABLE 6

| | | Component Rates | | |
|---|---|---|---|---|
| Stream Name | | PROD | PROD | PROD |
| Description | | End Reforming Catalyst in R1 | End Reforming Catalyst in R4 | End Reforming Catalyst in R4 |
| Phase | | Vapor | Vapor | Vapor |
| Temperature F. | | 950.000 | 950.000 | 950.000 |
| Pressure PSIA | | 214.696 | 214.696 | 214.696 |
| Molecular Weight | | 39.643 | 39.643 | 39.643 |
| Component Molar Rates | LB-MOL/HR | | | |
| Hydrogen | | 304.921 | 321.921 | 304.921 |
| Ethylbenzene | | 10.000 | 11.000 | 6.218 |
| Para-xylene | | 10.303 | 14.303 | 14.303 |
| Meta-xylene | | 23.609 | 31.609 | 31.609 |
| Ortho-xylene | | 11.809 | 15.809 | 15.809 |
| Others | | 166.971 | 149.971 | 157.753 |
| Total | LB-MOL/HR | 527.612 | 544.612 | 527.612 |

In comparing with Example 5, the results show that when the ethylbenzene conversion catalyst is located in the tail reactor (versus the lead reactor), the resulting reformate contains greater amounts of ethylbenzene.

What is claimed is:

1. A process for producing a reformate having reduced ethylbenzene content, said process comprising the steps of:
   (a) introducing a hydrocarbon feed containing precursors of ethylbenzene into a catalytic reforming unit comprised of a plurality of operatively connected reactors containing at least one lead reactor and a tail reactor;
   (b) reforming said feed in said at least one lead reactor under reforming conditions and in the presence of: (i) a first reforming catalyst; and, (ii) a catalyst effective for converting ethylbenzene to convert the precursors of ethylbenzene to ethylbenzene and to convert the ethylbenzene to xylene(s) and/or benzene; and,
   (c) further reforming at least a portion of the product of step (b) in said tail reactor under conversion conditions and in the presence of second reforming catalyst.

2. The process recited in claim 1, wherein said catalytic reforming unit is comprised of at least three operatively connected reactors.

3. The process recited in claim 2, wherein said at least one lead reactor comprises an upstream lead reactor and a downstream lead reactor and said catalyst effective for converting ethylbenzene is present in said upstream lead reactor.

4. The process recited in claim 2, wherein said at least one lead reactor comprises an upstream lead reactor and a downstream lead reactor and said catalyst effective for converting ethylbenzene is present in said downstream lead reactor.

5. The process recited in claim 2, wherein said at least one lead reactor comprises an upstream lead reactor and a downstream lead reactor and said catalyst effective for converting ethylbenzene is present in both the upstream lead reactor and the downstream lead reactor.

6. The process recited in claim 5, wherein the catalyst effective for converting ethylbenzene in said upstream lead reactor has a different mode for ethylbenzene conversion than the catalyst effective for converting ethylbenzene in said downstream reactor.

7. The process recited in claim 6, wherein the catalyst effective for converting ethylbenzene in said upstream lead reactor is effective for converting ethylbenzene to xylenes.

8. The process recited in claim 6, wherein the catalyst effective for converting ethylbenzene in said upstream lead reactor is effective for converting ethylbenzene to benzenes.

9. The process recited in claim 1, wherein said precursors of ethylbenzene are selected from the group consisting of $C_8$ isoalkane precursors of ethylbenzene, $C_8$ isoalkene precursors of ethylbenzene, and mixtures thereof.

10. The process recited in claim 9, wherein said precursors of ethylbenzene are selected from the group consisting of ethyl-cyclohexane, ethyl-cyclohexenes, 3-ethylhexane, 3-ethylhexenes, 3-ethylhexadienes, 3-ethylhexatriene, 3-methylheptane, 3-methylheptenes, 3-methylheptadienes, 3-methylheptatrienes, octane, octenes, octadienes, octatrienes, octatetraenes, and mixtures thereof.

11. The process recited in claim 10, wherein said precursors of ethylbenzene are present in said hydrocarbon feed in an amount from about 1 to about 10 weight percent based on the weight of said hydrocarbon feed.

12. The process recited in claim 1, wherein at least 25 percent of said ethylbenzene formed during the reforming of said hydrocarbon feed is converted.

13. The process recited in claim 1, wherein said hydrocarbon feed comprises $C_5$-205° C. naphtha.

14. The process recited in claim 1, wherein said precursors of ethylbenzene are present in said hydrocarbon feed in an amount from about 1 to about 5 weight percent based on the weight of said hydrocarbon feed.

15. The process recited in claim 1, wherein said first reforming catalyst, said second reforming catalyst, or both is a bifunctional catalyst.

16. The process recited in claim 1, wherein said first reforming catalyst, said second reforming catalyst, or both is a monofunctional catalyst.

17. The process recited in claim 16, wherein said monofunctional catalyst has a structure selected from the group consisting of LTL, FAU, *BEA, AEL, PAU, MAZ, MFI, MEL, MTW, OFF, EMT, MOR, MFS, EUO, MTT, HEU, FER, TON, and AFI.

18. The process recited in claim 16, wherein said monofunctional catalyst is selected from the group consisting of Silicalite 1, Silicalite 2, ALPO-5, zeolite L, zeolite X, zeolite Beta, zeolite Y, ETAS-10, ETGS-10, and ETS-10.

19. The process recited in claim 18, wherein said hydrocarbon feed contains $C_6$–$C_8$ hydrocarbons.

20. The process recited in claim 19, wherein said monofunctional catalyst comprises zeolite L and at least one Group VIII metal.

21. The process recited in claim 20, wherein said at least one Group VIII metal is platinum.

22. The process recited in claim 1, wherein said reforming is carried out at a temperature from about 300° C. to about 600° C., a pressure from about 446 kPa to about 3,549 kPa, a mole ratio of hydrogen to hydrocarbons from 0.1:1 to 10:1 and a liquid hour space velocity of between 0.1 and 20.

23. The process recited in claim 1, wherein said catalyst effective for converting ethylbenzene comprises an intermediate pore size molecular sieve.

24. The process recited in claim 23, wherein said catalyst effective for converting ethylbenzene has a structure selected from the group consisting of AEL, AFO, AHI, DAC, EPI, FER, HEU, LAU, MFI, TON, MTT, NES, MEL, EUO, and MFS.

25. The process recited in claim 23, wherein said catalyst effective for converting ethylbenzene is selected from the group consisting of ZSM-5, ZSM-11, ZSM-22, ZSM-23, ZSM-48, ZSM-50, ZSM-57, ZSM-58, EU-1, NU-87, SAPO-11, and SAPO-41.

26. The process recited in claim 25, where said catalyst effective for converting ethylbenzene further comprises at least one dehydrogenation/hydrogenation metal.

27. The process recited in claim 25, wherein said catalyst effective for converting ethylbenzene is selectivated to produce greater than equilibrium amounts of para-xylene versus the other xylene isomers.

28. The process recited in claim 27, wherein said catalyst effective for converting ethylbenzene is selectivated using an organosilicon compound.

29. The process recited in claim 28, wherein the resulting product contains greater than equilibrium amounts of para-xylene based on the total weight of xylenes present in said product.

30. The process recited in claim 1, wherein at least 50 weight percent of the ethylbenzene formed during the reforming of the hydrocarbon feed is converted.

31. The process recited in claim 25, where said catalyst effective for converting ethylbenzene further comprises a binder comprising particles of molecular sieve.

32. The process recited in claim 23, wherein said catalyst for converting ethylbenzene has an alpha greater than about 50.

33. The process recited in claim 25, wherein said catalyst for converting ethylbenzene is an aluminosilicate molecular sieve or gallosilicate molecular sieve.

34. The process recited in claim 1, wherein said ethylbenzene is converted to a product containing xylenes.

35. The process recited in claim 1, wherein said ethylbenzene is converted to a product containing benzene.

36. The process recited in claim 26, wherein said catalyst effective for converting ethylbenzene comprises ZSM-5.

37. The process recited in claim 26, wherein said ethylbenzene conversion catalyst is a zeolite bound zeolite catalyst comprising first crystals of MFI and a binder comprising second crystals MFI or MEL.

38. The process recited in claim 37, wherein said zeolite bound zeolite catalyst comprises first crystals of ZSM-5 and a binder of second crystals of Silicalite 1 or Silicalite 2.

39. The process recited in claim 1, wherein the reformate is cascaded over said ethylbenzene conversion catalyst.

40. A process for reforming a $C_5$-205° C. naphtha feed wherein at least 40 percent of the ethylbenzene formed during the reforming is converted to another product, said process comprising the steps of:

(a) introducing a $C_5$-205° C. naphtha feed containing $C_8$ isoalkane precursors of ethylbenzene, $C_8$ isoalkene precursors of ethylbenzene, or mixtures thereof into a catalytic reforming unit comprised of plurality of operatively connected reactors comprising at least one lead reactor and a tail reactor;

(b) reforming said feed in said at least one lead reactor under reforming conditions and in the presence of: (i) a first reforming catalyst; and, (ii) a catalyst effective for converting ethylbenzene and comprised of ZSM-5 to convert the precursors of ethylbenzene to ethylbenzene and to convert the ethylbenzene to xylene(s) and/or benzene; and, (c) further reforming at least a portion of the product of step (b) in said tail reactor under conversion conditions and in the presence of second reforming catalyst.

41. The process recited in claim 40, wherein said catalyst effective for converting ethylbenzene is selectivated using an organosilicon compound to produce greater than equilibrium amounts of para-xylene versus the other xylene isomers.

42. The process recited in claim 40, wherein said first reforming catalyst and said second reforming catalyst are bifunctional catalysts.

43. The process recited in claim 40, wherein said first reforming catalyst and said second reforming catalyst are monofunctional catalysts.

44. The process recited in claim 41, wherein the resulting product contains greater than equilibrium amounts of para-xylene based on the total weight of xylenes present in said product.

* * * * *